United States Patent [19]
Wallace et al.

[11] Patent Number: 5,508,179
[45] Date of Patent: Apr. 16, 1996

[54] USE OF DEOXYRIBOSE NICOTINAMIDE ADENINE DINUCLEOTIDE TO ENHANCE THE SPECIFICITY OF NAD$^+$-DEPENDENT LIGATION REACTIONS

[75] Inventors: Robert B. Wallace, Greenbrae; Hector Juarez-Salinas, Larksbur; Luis Ugozzoli, San Rafael, all of Calif.

[73] Assignee: Bio-Rad Laboratories, Inc., Hercules, Calif.

[21] Appl. No.: 214,636

[22] Filed: Mar. 18, 1994

[51] Int. Cl.$^6$ .................................................. C12P 19/34
[52] U.S. Cl. .................... 435/91.1; 435/91.2; 435/91.52; 435/6; 435/15; 435/810
[58] Field of Search ............................... 435/91.1, 91.2, 435/91.52, 810, 15, 18, 19, 21

[56] References Cited

PUBLICATIONS

Alvarez-Gonzales, R., "3'-Deoxy-NAD+ as a Substrate for Poly(ADP-ribose) polymerase and the Reaction Mechanism of Poly(ADP-ribose) Elongation," *The Journal of Biological Chemistry*, vol. 263, No. 33, pp. 17690–17696, (1988).
Alvarez-Gonzales, R., "Synthesis and Purification of Deoxyribose Analogues of NAD+ by Affinity Chromatography and Strong-Anion-Exchange High-Performance Liquid Chromatography," *Journal of Chromatography*, vol. 444, pp. 89–95, (1988).
Landergren, U., et al., "A Ligase-Mediated Gene Detection Technique," *Science*, vol. 241, pp. 1077–1080, (1988).
Van Brunt, J., "Amplifying Genes: PCR and its Alternatives," *Biotechnology*, vol. 8, pp. 291–294, (1990).
"Thermostable Enzymes, Ampligase® Thermostable DNA Ligase", *Epicentre Technologies*.
Wu, D. Y., and Wallace, R. B., "The Ligation Amplification Reaction (LAR)–Amplification of Specific DNA Sequences Using Sequential Rounds of Template–Dependent Ligation," *Genomics*, 4, 560–569 (1989).
Wu, D. Y. and Wallace, B. R., "Specificity of the nick–closing activity of bacteriophage T4 DNA ligase," *Gene*, vol. 76, pp. 245–254, (1989).
Engler, M. J. and Richardson, C. C., "DNA Ligases," *The Enzymes*, vol. XV, Chapter 1, pp. 3–29, (1982).
Martinez et al., *Biochem. Biophys. Res. Comm.* 181(3), 1412–1418 (1991).
Pedrhza–Reyes et al., *FEBS LETT.* 277(1,21, 88–92 (1990).
Alvarez-Gonzalez et al., *Biochemistry* 27, 5378–5383 (1988).

*Primary Examiner*—W. Gary Jones
*Assistant Examiner*—Kenneth R. Horlick
*Attorney, Agent, or Firm*—Townsend and Townsend and Crew

[57] ABSTRACT

This invention provides methods and compounds relating to the use of deoxyribose nicotinamide adenine dinucleotide (dNAD$^+$) analogues in NAD$^+$-dependent ligation reactions. The compounds and methods may be used in NAD$^+$-dependent ligation reactions generally, and to increase the specificity of NAD$^+$-dependent ligation reactions.

20 Claims, 4 Drawing Sheets

USE OF DEOXYRIBOSE NICOTINAMIDE ADENINE DINUCLEOTIDE TO ENHANCE THE SPECIFICITY OF NAD⁺-DEPENDENT LIGATION REACTIONS

BACKGROUND OF THE INVENTION

The ligation of polymerized nucleic acids is a necessary step in the fundamental techniques of molecular biology. Ligation of deoxyribonucleic acid (DNA) polymers is ubiquitous in cloning, sequencing and analyzing genetic material. There are several general texts which describe ligation generally, including Sambrook et al., Molecular Cloning—A Laboratory Manual (2nd Ed.), Vol. 1–3, Cold Spring Harbor Laboratory, Cold Spring Harbor, N.Y., 1989 (hereinafter "Sambrook").

Techniques utilizing ligation are becoming increasingly important as general tools of basic research and in clinical settings. The ligation chain reaction (LCR; sometimes denoted the "ligation amplification reaction" or "LAR") and related techniques are of increasing utility, particularly as diagnostic tools. LCR (described below) provides a mechanism for linear or exponential amplification of a target nucleic acid via ligation of adjacent oligonucleotides. This amplification may be performed to distinguish target nucleic acids which differ by a single nucleotide, providing a powerful tool for the diagnosis of genetic disease, the analysis of genetic variation, and the detection of specific DNA sequences. A problem of ligation generally, and of LCR in particular is a lack of specificity in the ligation reaction. Undesired ligation products increase the percentage of undesired constructs to desired constructs or "noise" in the cloning process, and increase the noise to signal ratio in LCR, limiting the analytic ability of the technique.

The present invention overcomes the limitations of the prior art by increasing substantially the specificity of ligation. The increase in specificity is achieved by substitution of deoxyribose NAD⁺ for NAD⁺ as a cofactor in NAD⁺-dependent ligation reactions. Examples of ligase enzymes used in ligation reactions which require NAD⁺ as a cofactor include $E.\ coli$ DNA ligase and Taq DNA ligase, each of which displays an increase in the specificity of ligation upon the addition of β-2'-deoxyribose NAD⁺ or β-3'-deoxyribose NAD⁺.

SUMMARY OF THE INVENTION

The present invention provides methods for ligating nucleic acid oligomers, wherein the methods comprise incubation of an nicotinamide adenine dinucleotide-dependent nucleic acid ligase and said nucleic acid oligomers in the presence of deoxyribose nicotinamide adenine dinucleotide. Examples of the deoxyribose nicotinamide adenine dinucleotide which may be used in the methods of the present invention include β-2'-deoxyribose nicotinamide adenine dinucleotide and β-3'-deoxyribose NAD⁺. Examples of nucleic acid ligase enzymes which may be used in the methods of the present invention include Taq DNA Ligase (New England Biolabs, Beverly Mass.), $E.\ Coli.$ DNA ligase (MBR Molecular Biology Resources Inc., Milwaukee Wis.), Ampligase® (Epicentre Technologies, Madison Wis.) and TTh (Stratagene Cloning Systems, La Jolla Calif.).

The present invention further provides methods wherein the nucleic acid oligomers are hybridized to complementary target nucleic acids prior to ligation. The nucleic acid oligomers used in the methods of the present invention may be repetitively hybridized to complementary target nucleic acids, ligated, and dissociated from the complementary nucleic acids. Multiple sets of nucleic acid oligomers may be used in the ligation reactions of the present invention, including a set of nucleic acid oligomers complementary to a target nucleic acid sequence, and a set of nucleic acid oligomers which are complementary to the target-complementary nucleic acid oligomers. The use of a combination of oligomers complementary to target and target complementary nucleic acid oligonucleotides allows the methods of the present invention to achieve geometric amplification of a target polynucleotide in conjunction with LCR.

The present invention provides an improvement over existing ligation methods comprising the addition of deoxyribose nicotinamide adenine dinucleotide to a typical aqueous ligation solution. The improvement may comprise e.g., the addition of β-2'-deoxyribose nicotinamide adenine dinucleotide, or β-3'-deoxyribose nicotinamide adenine dinucleotide to the aqueous ligation solution. Examples of ligase enzymes, possible oligonucleotide combinations and typical uses for the improvement are described above.

The present invention further provides for kits for ligating DNA oligomers wherein the kits include a container containing an nicotinamide adenine dinucleotide-dependent DNA ligase and deoxyribose nicotinamide adenine dinucleotide. Examples of the nicotinamide adenine dinucleotide-dependent DNA ligase which may be used in the kit of the present invention include the ligases mentioned above. Furthermore, one of skill will readily recognize that the kits may possess compartments containing additional items such as instructional materials and aqueous ligation buffers. The kits may also contain oligonucleotides complementary to target sequences encoding a protein which serves as a diagnostic marker for a genetic mutation, such as Sickle-Cell Anemia.

DEFINITIONS

"Amplification" refers to the process of creating multiple copies of a DNA sequence, which may be achieved e.g., by PCR, LCR, TAS, 3SR, QB, or standard cloning methodologies.

"Aqueous Ligation Solution" refers to an aqueous solution which contains salt conditions (e.g., the presence of KCl and NaCl) in amounts which are close enough to physiological norms for the ligase used in the reaction to permit the ligase to function.

"DNA" refers to deoxyribonucleic acid. Nucleotides are phosphate esters of nucleosides which are acidic due to the hydroxy groups on the phosphate. The polymerized nucleotides deoxyribonucleic acid (DNA) and ribonucleic acid (RNA) store the genetic information which controls all aspects of an organism's interaction with its environment. The nucleosides of DNA and RNA are connected via phosphate units attached to the 3 position of one pentose and the 5 position of the next pentose; thus they are phosphodiesters. In the present invention, DNA and RNA may be derived from biological sources or produced synthetically.

"Oligonucleotide" refers to a nucleic acid sequence composed of two or more nucleotides. An oligonucleotide can be derived from natural sources but is often synthesized chemically. It may be of any length. It may be used as a primer, a probe or a component of a ligation reaction.

Figure 1:
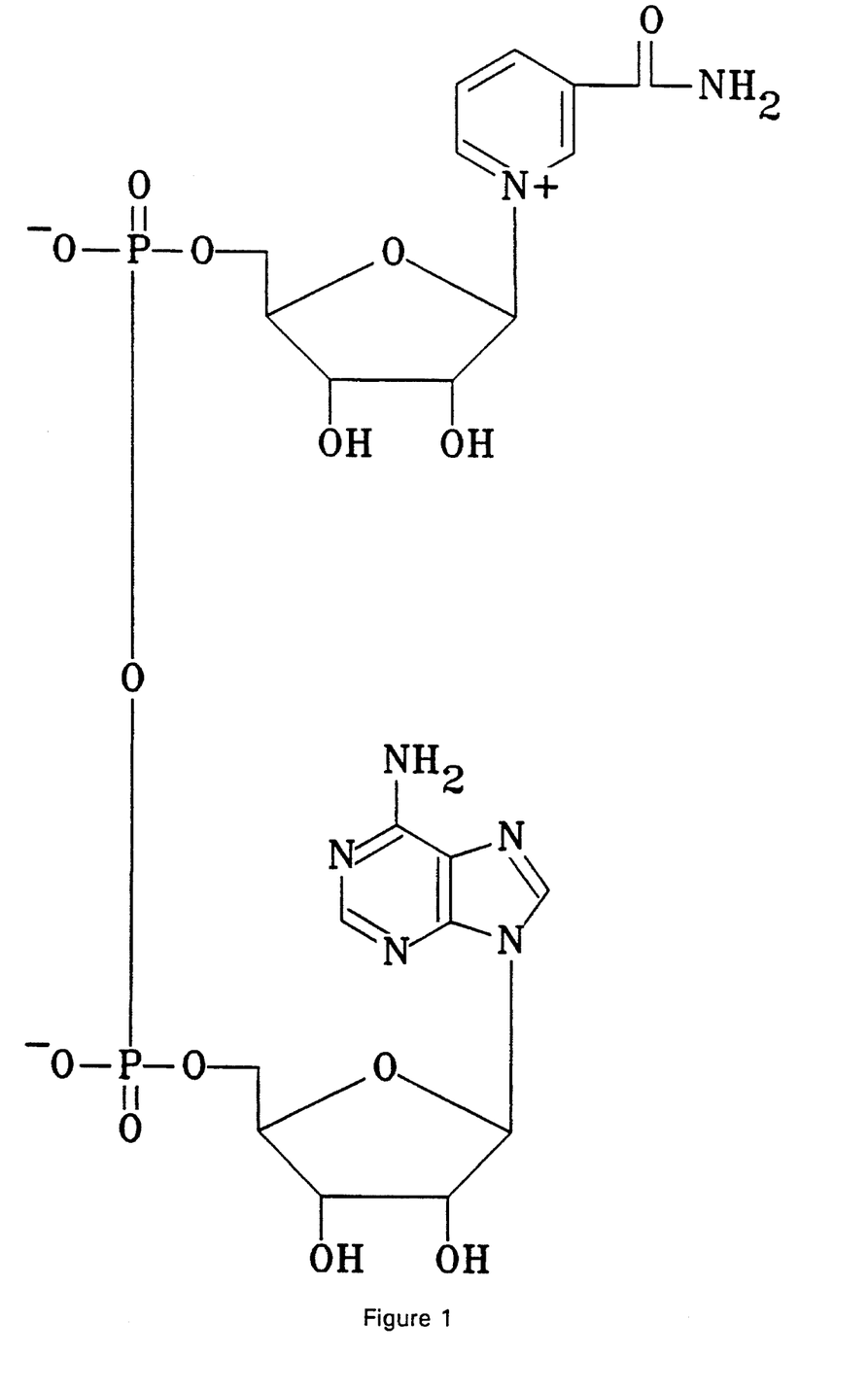
FIG. 1 shows the chemical structure of β-nicotinamide adenine dinucleotide.
Figure 2:
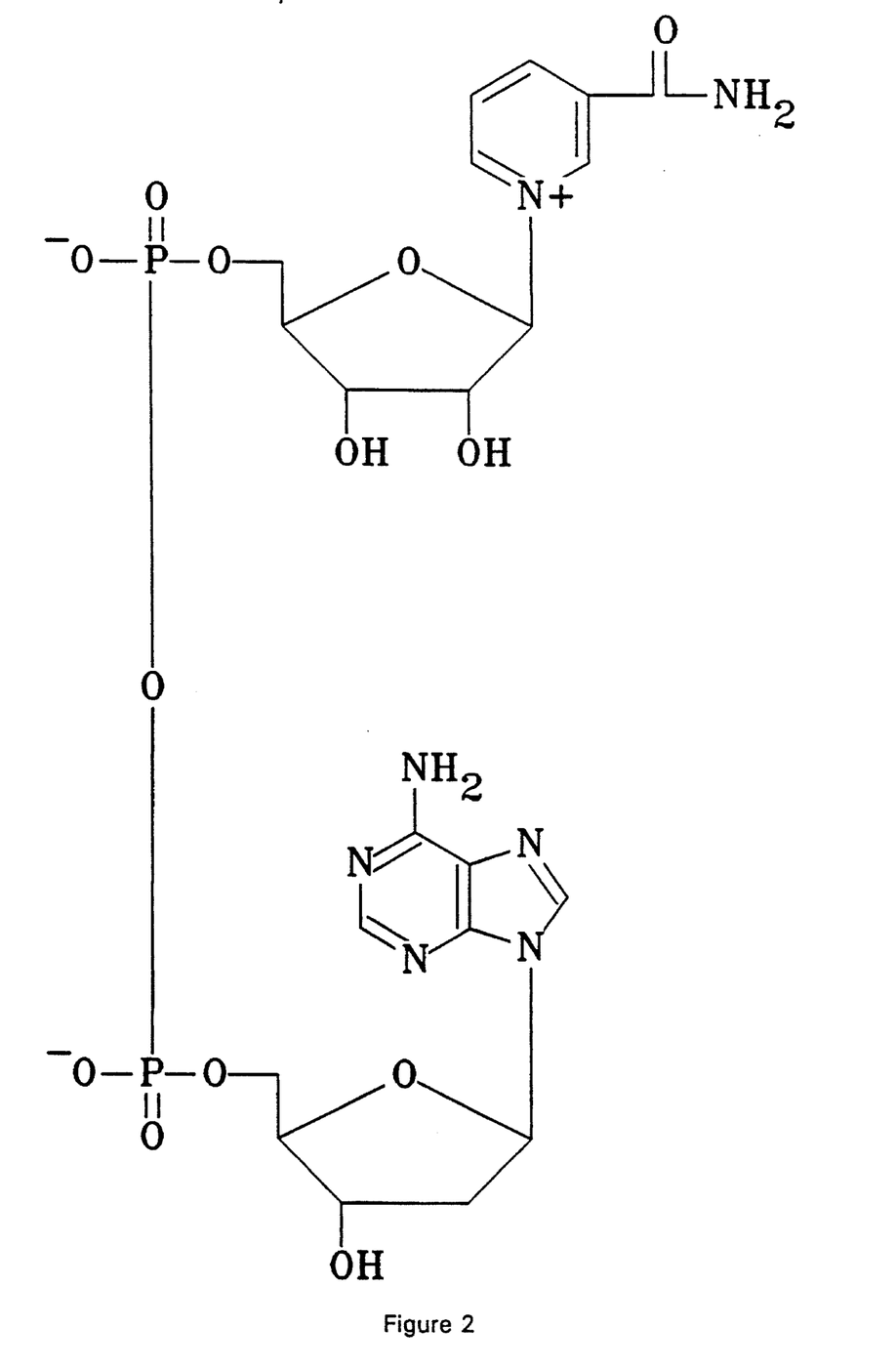
FIG. 2 shows the chemical structure of β-2'-nicotinamide adenine dinucleotide.
Figure 3:
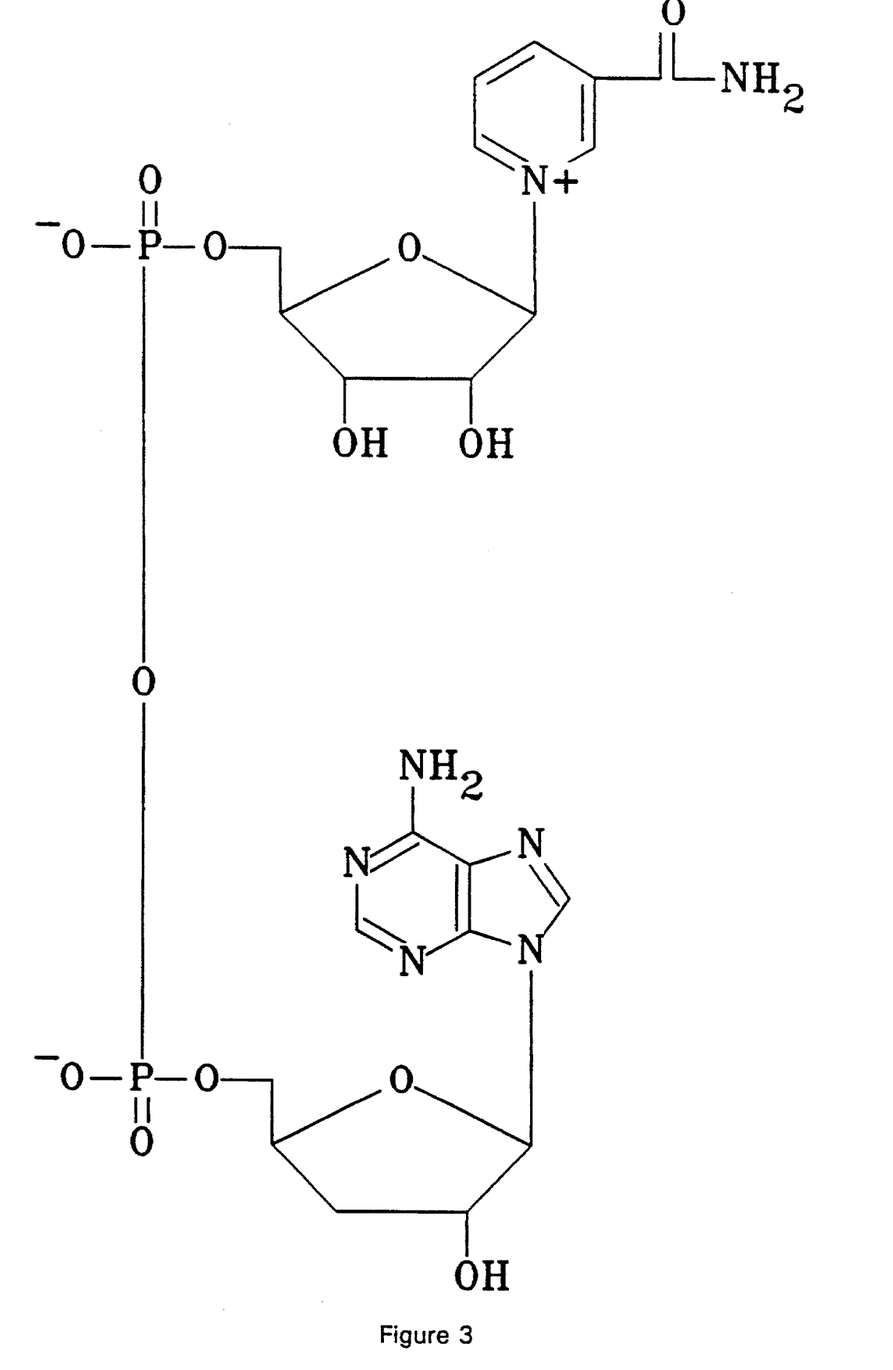
FIG. 3 shows the chemical structure of β-3'-nicotinamide adenine dinucleotide.

"$NAD^+$" refers to nicotinamide adenine dinucleotide. When reduced, the molecule becomes NADH. Related molecules include nicotinamide adenine dinucleotide phosphate ($NADP^+$ or NADPH when reduced) wherein a phosphate group is connected to the adenosine ribose of $NAD^+$. The chemical structure of $NAD^+$ and two related analogues, β-2'-deoxyribose nicotinamide adenine dinucleotide (2'dNAD) and β-3'-deoxyribose nicotinamide adenine dinucleotide (3'dNAD) are shown in FIGS. 1–3.

"Phosphorylation" refers to the introduction of a phosphoryl group into a compound through the formation of an ester bond between the compound and phosphoric acid.

"Sequence identity" in this application denotes two nucleic acid sequences which are either the same, or which when one is the complement of the other will be sufficiently complementary for the two strands to bind with a high degree of specificity under physiological conditions.

"Target nucleic acid" or "target sequence" refers to a sequence or fragment of DNA or RNA to be amplified.

DETAILED DESCRIPTION

The present invention provides a means of increasing the specificity of $NAD^+$-dependent ligation reactions. The increase in specificity is achieved by substituting deoxyribose $NAD^+$ analogues for $NAD^+$ as a cofactor in ligation reactions catalyzed by $NAD^+$-dependent DNA ligase enzymes. Particularly preferred deoxyribose $NAD^+$ analogues include β-2'-deoxyribose $NAD^+$ ($2'dNAD^+$) and β-3'-deoxyribose $NAD^+$ ($3'dNAD^+$). The $NAD^+$-dependent ligase enzymes used in practicing the present invention may be derived from natural sources, or may be produced synthetically, e.g., by purification of the ligase from a bacterium into which the DNA encoding the ligase is cloned. Particularly preferred $NAD^+$-dependent ligase enzymes include commercially available variants of Taq DNA ligase. The increase in the specificity of ligation resulting from the present invention is useful for any process where increased specificity of ligation is desirable, including cloning and in vitro diagnostic assays. The present invention will be particularly useful for increasing the specificity of LCR reactions.

GENERAL METHODS

The present invention, which provides a means of increasing the specificity of $NAD^+$-dependent ligation reactions has broad utility, and may be used in conjunction with many well-known techniques such as LCR, PCR, cloning, TAS, 3SR and QB amplification. The following discussion of general methods which may be used in conjunction with the present invention is intended for illustrative purposes. It is expected that one of skill will recognize many alternative methods to those discussed as being sufficient to practice the invention.

Synthesis and Purification of $NAD^+$ analogues.

The synthesis and purification of deoxyribose $NAD^+$ analogues useful in the present invention is known in the art. $NAD^+$ is available from a variety of commercial sources, such as Sigma Chemical Co, St. Louis Mo. The synthesis of β-2'-deoxyribose $NAD^+$ ($2'dNAD^+$) and β-3'-deoxyribose $NAD^+$ ($3'dNAD^+$) have been described previously, and one of skill will recognize that variant methods for the preparation of $2'dNAD^+$ and $3'dNAD^+$ may be employed. See Alvarez-Gonzales et al. (1988) *Biochemistry* 27, 5378–5383; Alvarez-Gonzales (1988) *Journal of Chromatography* 444, 89–95; Martinez et al. (1991) *Biochemical and Biophysical Research Communications* 1412–1418, and Alvarez-Gonzales The *Journal of Biological Chemistry* (1988) 17690–17696. Briefly, 2'-deoxy ATP (2-dATP) or 3' deoxy ATP (3-dATP) are incubated at a concentration of 0.5 mM for approximately 2 hours in glycylglycine buffer containing 100 mM glycylglycine (pH 7.4), 10 mM $MgCl_2$, 3.0 mM nicotinamide mononucleotide ($NMN^+$), 3 units of inorganic pyrophosphatase and 0.2 units of $NAD^+$ pyrophosphoralase in a reaction volume of e.g., 2 ml (all of the reaction components are commercially available from, e.g., Sigma Chemical Co., St. Louis Mo.). The reaction is stopped by cooling the mixture to 0° C. The unreacted dATP is then removed by e.g., loading the reaction mix onto a 2 ml boronate affi-gel 601 column (Bio-Rad laboratories Inc., Richmond, Calif.). The column is washed with 10 ml of ammonium formate (pH 9.0), and eluted with 10 ml of ammonium formate (pH 5.0). The eluate is then lyophilized. The lyophilized material may be stored until use, or redissolved in a small volume of $H_2O$ and stored at $-20°$ C. The $2'dNAD^+$ or $3'dNAD^+$ may be further purified by various chromatographic methods such as HPLC.

Alternatively, the following strategy may be used to produce 2' or 3'NAD. A 1 ml mixture containing 0.2 units of NAD pyrophosphorylase, 3 units of inorganic pyrophosphatase (each commercially available from, e.g., Boheringer Mannheim, Germany), 20 mM $MgCl_2$, 3 mM NMN, 1 mM 2' or 3' deoxyadenosine 5' triphosphate, and 100 mM Glycyl-Glycine buffer, pH 7.4. (each commercially available from e.g., Sigma, St. Louis, Mo.) is incubated for approximately 16 hours (overnight) at 37° C. After incubation, 0.5 ml of 1M ammonium acetate buffer pH 8.8 (e.g., from Sigma) is added and the sample is applied to a glass column containing 2 ml of Bio-Gel 601 (commercially available from BioRad Laboratories, Hercules, Calif.) previously equilibrated with 1M ammonium acetate buffer, pH 8.8. The column is washed with 1M ammonium acetate buffer, pH 8.8, until all unbound UV absorbent material (measured at 260 nm) has eluted out of the column, including the unused deoxyadenosine 5' triphosphate and enzymes. The column in then washed with a 0.2M ammonium acetate buffer, pH 4, and the UV absorbent peak (260 nm) containing unused NMN and synthesized dNAD is collected. The collected material is applied to a Bio Sil ODS 5S HPLC column (e.g., from BioRad) previously equilibrated with 0.1M TEAA (triethylamine acetate) buffer, pH 7 (Commercially Available from e.g., Glenn Research, Sterling, Va.) and the unbound UV absorbent material (260 nm) containing unused NMN is discarded. A 30 min gradient of 0 to 25% acetonitrile (commercially available from, e.g., EM Sciences, Gibbstown, N.J.) is then run and the (bound) peak containing pure dNAD is collected. The TEAA/Acetonitrile buffer is then evaporated and the dried sample is dissolved in an appropriate volume of water and the UV absorbance at 260 nm is measured to determine yield.

Ligase-mediated Gene Detection Techniques

The present invention provides a method for increasing the specificity of the ligation reaction using an $NAD^+$-dependent DNA ligase enzyme. $NAD^+$-dependent DNA ligases catalyze the formation of phosphodiester bonds in polynucleic acids. The polynucleic acids are generally double-stranded and ligation is most efficiently performed when the double-stranded polynucleic acids (e.g., DNA or heteroduplex RNA:DNA) contain complementary protruding 5' or 3' termini. However, NAD⁺-dependent ligases can accomplish ligation between polynucleic acids containing blunt or mis-matched termini. In some applications, the blunt or mis-match ligation products may be desirable, in which case volume excluders such as polyethylene glycol are typically added to encourage the ligation, or T4 DNA ligase (which does not require NAD⁺ to catalyze ligation) is used in place of the more selective NAD⁺-dependent polynucleotide ligases. The present invention reduces the ability of NAD⁺-dependent polynucleotide ligases to ligate blunt or mismatched polynucleotide termini, and is therefore useful whenever blunt or mis-matched ligation products are undesirable.

The ability to prevent blunt or mis-matched ligation products is particularly desirable in the LCR reaction and related gene-detection techniques. LCR and several related gene techniques are well known in the art. See Landegren et al., (1988) *Science* 241, 1077–1080; Wu and Wallace, (1989) *Gene* 76, 245–254; Van Brunt (1990) *Biotechnology* 8, 291–294; Wu and Wallace, (1989) *Genomics* 4, 560–569; Barringer et al., (1990) *Gene* 89, 117 *The Journal Of NIH Research* (1991) 3, 81–94; and Carr, European patent No. 0246864. LCR may be used for linear or exponential amplification of a target polynucleotide. The principle underlying LCR is straightforward: Oligonucleotides which are complementary to adjacent segments of a target polynucleotide are brought into proximity by hybridization to the target, and ligated using a ligase. To achieve linear amplification of the target polynucleotide, a single pair of oligonucleotides which hybridize to adjoining areas of the target sequence are employed: the oligonucleotides are ligated, denatured from the template and the reaction is repeated. To achieve exponential amplification of the target polynucleotide, two pairs of oligonucleotides (or more) are used, each pair hybridizing to complementary sequences on e.g., a double-stranded target polynucleotide. After ligation and denaturation, the target and each of the ligated oligonucleotide pairs serves as a template for hybridization of the complementary oligonucleotides to achieve ligation. The ligase enzyme used in performing LCR is typically thermostable, allowing for repeated denaturation of the template and ligated oligonucleotide complex by heating the ligation reaction.

LCR is useful as a diagnostic tool in the detection of genetic disease, and in the analysis of genetic variation. Using the methods described above, it is possible to distinguish between target polynucleotides which differ by a single nucleotide at the site of ligation. Ideally, ligation occurs only between oligonucleotides hybridized to a target polynucleotide where the complementarity between the oligonucleotides and the target is perfect, enabling differentiation between allelic variants of a gene. In practice, however, ligase enzymes are non-specific enough that substantial non-specific ligation (i.e., ligation of oligonucleotides which are not fully complementary to a target polynucleotide at the site of ligation) occurs during LCR. The specificity of ligation during LCR was initially increased by substituting the more specific NAD⁺-dependent ligases such as *E. coli* ligase and (thermostable) Taq ligase for the less specific T4 DNA ligase. However, even the relatively specific NAD⁺-dependent ligases display substantial non-specific ligation. The present invention replaces NAD⁺ in NAD⁺-dependent ligation reactions with deoxyribose NAD⁺ analogues such as β-2'-deoxyribose NAD⁺ and β-3'-deoxyribose NAD⁺, limiting the ability of NAD⁺-dependent polynucleotide ligases to ligate blunt or mis-matched termini, thereby increasing the specificity of LCR.

Cloning, PCR, TAS, 3SR, And QB Amplification

The present invention can be used in conjunction with other techniques such as PCR, TAS, 3SR, QB amplification and cloning, whenever a person of skill desires an increase in the specificity of the ligation products from a ligation step associated with the relevant technique. All of the enumerated techniques are well-known in the art, and the following discussion is for illustrative purposes only.

(1). Cloning.

The ligation techniques of the present invention may be utilized for amplification of a target segment of polynucleotide (either DNA or RNA) through cloning. Cloning is a general term for the amplification of a desired segment of a polynucleotide in a biological host. A wide variety of cloning methodologies are well-known to persons of skill. Examples of these techniques and instructions sufficient to direct persons of skill through many cloning exercises may be found in Berger and Kimmel, *Guide to Molecular Cloning Techniques, Methods in Enzymology* 152 (Academic Press, Inc., San Diego, Calif.) (hereinafter "Berger") or in Sambrook. General techniques for shuttling DNA between prokaryotes and eukaryotes are described in Cashion et al., U.S. Pat. No. 5,017,478. The "drop in" or "gap filling" cloning method is described in Carr, European Patent No. 0,246,864.

The ligation products of the present invention can be cloned into a desired vector and amplified, or the ligation methods of the present invention may be combined with in vitro amplification techniques as described above to produce an amplicon for cloning. Inasmuch as cloning often involves the ligation of a target DNA segment into a replicable vector, the present invention provides a mechanism for increasing the proportion of desirable ligation products, thereby simplifying many cloning exercises.

(2). PCR

The ligation methods of the present invention may be combined with PCR to produce target polynucleotides for subsequent cloning, sequencing or diagnostic analysis. PCR may be performed on separate DNA sequences followed by ligation of the PCR products using the methods of the present invention. Conversely, PCR may be performed on the ligation products generated using the present invention. In either case, the final product may be assayed for the presence or absence of a sequence of interest, or cloned for further analysis. PCR products may be analyzed for the presence of specific sequences using LCR.

The use of the polymerase chain reaction (PCR) (Mullis et al., (1987) U.S. Pat. No. 4,683,202) in the field of molecular biology is well known. PCR has been adapted for many diverse purposes, including cloning, sequencing, forensics, diagnostics and cladistic analysis. The technique is detailed in several general sources which provide adequate guidance to one of skill to perform the technique, including Sambrook and PCR *Protocols A Guide to Methods and Applications* (Innis et al. eds) Academic Press Inc. San Diego, Calif. (1990) (hereinafter "Innis"). Also see Arnheim & Levinson (Oct. 1, 1990) C&EN 36–47.

(3). TAS, 3SR and QB amplification

The ligation methods of the present invention may also be practiced in conjunction with other in vitro amplification techniques such as the transcription-based amplification system (TAS), the self-sustained sequence replication system (3SR) and the Qβ replicase amplification system (QB), all of which are reviewed in *The Journal Of NIH Research*

(1991) 3, 81–94. The present invention may be practiced in conjunction with TAS (Kwoh, et al. (1989) *Proc. Natl. Acad. Sci. USA* 86, 1173 or the related 3SR (Guatelli et al. (1990) *Proc. Natl. Acad. Sci. USA* 87, 1874) for detecting single-base alterations in target nucleic acids by transcribing the target, annealing oligonucleotide primers to the transcript and ligating the annealed primers. QB replication (Lomell et al. (1989) *J. Clin. Chem* 35, 1826) may also be used in conjunction with the ligation methods of the present invention to detect genetic variation by performing QB amplification on DNA ligated by the methods of the present invention.

Oligonucleotide Synthesis

The present invention may be utilized with DNA or RNA as a template in the ligation reaction as described above. The polynucleic acid target may be derived from naturally occurring sources, or may be created synthetically. The oligonucleotides used in LCR may be derived from natural sources, e.g., by digesting plasmid DNA with a restriction enzyme and gel-purifying the desired DNA fragment, or may be created synthetically. Polynucleotide synthesis from commercially available phosphoramidites may be carried out on commercially available solid phase oligonucleotide synthesis machines (Needham-VanDevanter, D. R., et al., *Nucleic Acids Res.*, 12:6159–6168 (1984) ) or chemically synthesized using the solid phase phosphoramidite triester method described by Beaucage et al. (Beaucage et al., *Tetrahedron Letts.* 22 No. 20:1859–1862 (1981). Purification of oligonucleotides can be performed, e.g., using reverse phase or anion-exchange HPLC or by denaturing or native acrylamide gel electrophoresis.

The following examples are provided by way of illustration only and not by way of limitation, Those of skill will readily recognize a variety of noncritical parameters which could be changed or modified to yield essentially similar results.

EXAMPLES

Example 1: The LCR reaction using β-2'-deoxyribose $NAD^+$ as a cofactor with synthetic target DNA.

To demonstrate that β-2'-deoxyribose $NAD^+$ ($2'dNAD^+$) works as a cofactor for thermostable DNA Ligase, and that LCR shows enhanced specificity using $2'dNAD^+$ as a cofactor, two different thermostable DNA ligases (Ampligase® Thermostable DNA Ligase, Epicentre Technologies, Madison Wis., and Taq DNA Ligase, NE Biolabs, Beverly Mass.) were used to perform LCR. In each case, $2'dNAD^+$ was shown to serve as a cofactor for the $NAD^+$-dependent ligase enzymes, and in each case the use of $2'dNAD^+$ served to increase the specificity of the ligation reactions (see Table 2 below).

To further demonstrate that $2'dNAD^+$ functions as a cofactor for a wide variety of $NAD^+$-dependent ligase enzymes, the thermostable, highly-specific ligase enzymes Taq DNA Ligases from MBR Molecular Biology Resources Inc. (Milwaukee, Wis.) and TTh from Stratagene Cloning Systems (La Jolla, Calif.) were shown to accept $2'dNAD^+$ as a substrate for ligation. The enzyme Taq from MBR refers to a ligase which is distinct from the enzyme Taq as supplied from N.E. Biolabs. Taq (MBR) and TTh provide for highly specific ligation using $NAD^+$ as a cofactor, and no additional specificity is conferred by the use of $2'dNAD^+$ as a cofactor. This was expected, as the specificity conferred by the enzymes Taq (MBR) and TTh using $NAD^+$ as a cofactor are essentially at the limits of detection using the techniques described below. The results for Taq (MBR) and TTh demonstrate the broad utility of $2'dNAD^+$ as a cofactor for ligase enzymes. The following details the methodology used in demonstrating the ability of $2'dNAD^+$ to serve as a cofactor in $NAD^+$-dependent ligation reactions.

The target DNA amplified in the LCR reactions was synthetic DNA corresponding to either the normal ($β^A$) allele for the β-chain of the human hemoglobin gene, or the allele of hemoglobin corresponding to sickle cell hemoglobin ($β^S$). For each thermostable DNA ligase, specificity was assayed by ligation of the primers complementary to the normal $β^A$ DNA sequence (MD074, and MD073: see Table 1) in the presence of either $β^A$ or $β^S$ synthetic DNA templates and by ligation of $β^S$-complementary oligonucleotide primers (MD076, and MD074: see Table 1) in the presence of either $β^A$ or $β^S$ synthetic templates. The synthetic duplexes were prepared by incubating equimolar amounts of $β^A$ and $β^A$ complementary oligonucleotide primers or $β^S$ and $β^S$ complementary oligonucleotide primers at 90° C. for 5 minutes and followed by a room temperature incubation for 25 minutes. The duplexes were subsequently purified on a 10% polyacrylamide gel.

Primer MD074 was 5' end-labeled with [$γ^{32}P$] ATP and T4 polynucleotide kinase, and primers MD073, and MD076 were 5'-phosphorylated with T4 DNA polynucleotide kinase and ATP. Reactions were performed in a 25 μl volume containing 20 mM Tris-HCl pH 7.9, 25 mM KCl, 10 mM $MgCl_2$, 0.1% Triton, 3.3 units of thermostable DNA Ligase, 10 fmol of synthetic DNA duplex template, 100 fmol of each ligation primer, and 200 μM $2'dNAD^+$ or 200 μM $NAD^+$. The samples were incubated for 2 minutes at 94° and then for 30 minutes at 62° C. in an Ericomp thermocycler. After incubation, 3 μl of each sample were mixed with 7 μl of denaturing loading buffer (90% formamide, 1×TBE, 0.1% (weight/volume) xylene cyanol, 0.1% (weight/volume) bromophenol blue) incubated 2 minutes at 70° C. and analyzed on a denaturing 7M urea 10% polyacrylamide gel. The gel was scanned with a Bio-Rad GS 250 Molecular Imager. The ligated DNA fragment was quantitated by determining the height of the peak in a 1 dimensional profile scan in pixel density units. The results are shown in Table 2. The $2'dNAD^+$ functions as a cofactor for all four $NAD^+$-dependent ligase enzymes. The substitution of $2'dNAD^+$ for $NAD^+$ as a cofactor in the ligation reaction confers enhanced specificity upon Ampligase (Epicentre technologies) and Taq ligase (NE biolabs). Table 2 shows that the ratio of ligation for matched to mis-matched oligonucleotides for Ampligase (Epicenter) using $2'dNAD^+$ is approximately 5 times as high as the ratio of ligation for matched to mis-matched oligonucleotides using $NAD^+$ as a cofactor. Similarly, the ratio for Taq ligase (N.E. biolabs) shows a 4.6 fold improvement by the substitution of $2'dNAD^+$ for $NAD^+$. The data indicates that the invention works especially well where mismatch ligations are most frequent.

TABLE 1

Sequences of primers used in Examples 1–6

| Primer | Seq. Id. No. | Sequence (5' to 3') |
|---|---|---|
| MD074 | 1 | ACATGGTGCACCTGACTCCTG |
| MD073 | 2 | AGGAGAAGTCTGCCGTTACTTTTGGCACTGGCCGTCGTTTTAC |
| MD075 | 3 | CAGGAGTCAGGTGCACCATGTT-Biotin |
| MD076 | 4 | TGGAGAAGTCTGCCGTTACTTTTGGCACTGGCCGTCGTTTTAC |
| MD077 | 5 | CAGTAACGGCAGACTTCTCCT |
| MD078 | 6 | CAGTAACGGCAGACTTCTCCA |
| MD119 | 7 | AGGAGAAGTCTGCCGTTACTTT |
| MD120 | 8 | TGGAGAAGTCTGCCGTTACTTT |
| MD121 | 9 | TGGCACTGGCCGTCGTTTTACTTCATGGTGCACCTGACTCCTG |
| MD102 | 10 | TGGCACTGGCCGTCGTTTTACTTCACTAACGGCAGACTTCTCCT |
| MD103 | 11 | TGGCACTGGCCGTCGTTTTACTTCAGTAACGGCAGACTTCTCCA |
| $\beta^{AA}$ | 12 | AACAGACACCATGGTGCACCTGACTCCTGAGGAGAAGTCTGCCGTTACTGCC-CTGTGGGG |
| $\beta^{AA}$ com. | 13 | CCCCACAGGGCAGTAACGGCAGACTTCTCCTCAGGAGTCAGGTGCACCATGG-TGTCTGTT |
| $\beta^{SS}$ | 14 | AACAGACACCATGGTGCACCTGACTCCTGTGGAGAAGTCTGCCGTTACTGCC-CTGTGGGG |
| $\beta^{SS}$ com. | 15 | CCCCACAGGGCAGTAACGGCAGACTTCTCCACAGGAGTCAGGTGCACCATGG-TGTCTGTT |
| UP-AP* | 16 | GTAAAACGACGGCCAGTGCCA |

*Commercially Available from BioRad Laboratories, Inc. (Richmond, CA) Catalogue #170-3588

TABLE 2

Substitution of NAD$^+$ by 2'dNAD$^+$ (Example 1).

| | | | | | Ligated Product (Pixel Density Units) | |
|---|---|---|---|---|---|---|
| DNA ligase | Source | Template | Oligonucleotides | M or MM** | NAD$^+$ | 2'dNAD$^+$ |
| Taq*** | MBR | $\beta^A$ | MD074-MD073 | M | 868 | 620 |
| Taq | MBR | $\beta^S$ | MD074-MD073 | MM | 16 | 12 |
| Taq | MBR | $\beta^A$ | MD074-MD076 | MM | 40 | 40 |
| Taq | MBR | $\beta^S$ | MD074-MD076 | M | 880 | 464 |
| Ampligase | Epicenter | $\beta^A$ | MD074-MD073 | M | 1320 | 936 |
| Ampligase | Epicenter | $\beta^S$ | MD074-MD073 | MM | 864 | 44 |
| Ampligase | Epicenter | $\beta^A$ | MD074-MD076 | MM | 800 | 184 |
| Ampligase | Epicenter | $\beta^S$ | MD074-MD076 | M | 1728 | 1128 |
| TTh**** | Stratagene | $\beta^A$ | MD074-MD073 | M | 944 | 336 |
| TTh | Stratagene | $\beta^S$ | MD074-MD073 | MM | 40 | 24 |
| TTh | Stratagene | $\beta^A$ | MD074-MD076 | MM | 20 | 20 |
| TTh | Stratagene | $\beta^S$ | MD074-MD076 | M | 936 | 224 |
| Taq | NE Biolabs | $\beta^A$ | MD074-MD073 | M | 848 | 752 |
| Taq | NE Biolabs | $\beta^S$ | MD074-MD073 | MM | 192 | 28 |
| Taq | NE Biolabs | $\beta^A$ | MD074-MD076 | MM | 356 | 68 |
| Taq | NE Biolabs | $\beta^S$ | MD074-MD076 | M | 1044 | 768 |

**M = matched (base-paired) and MM-mismatched at ligation junction
***"Taq" from MBR refers to a ligase which is distinct from the ligase "Taq" from N.E. Biolabs.
****TTh and Taq (MBR) show high specificity using either NAD$^+$ or 2'dNAD$^+$ as cofactors in the ligation reaction.

Example 2: The LCR reaction using β-2'-deoxyribose NAD$^+$ as a cofactor with genomic DNA Templates.

To demonstrate that 2'dNAD$^+$ confers enhanced specificity upon NAD$^+$-dependent ligases such as Taq ligase (N.E. biolabs) using genomic DNA as a target polynucleotide for amplification during LCR, reactions for each cofactor were carried out as described below. The results also demonstrate that 2'dNAD$^+$ reduces the rate of undesirable blunt-ended (i.e., template-independent) ligation when used as a cofactor during LCR.

LCR reactions were performed in 25 μl reactions containing 20 mM Tris-HCl pH 7.9, 25 mM KCl, 10 mM MgCl$_2$, 200 μM 2'dNAD$^+$ (or 1 mM NAD$^+$), 6.8 units of Taq Ligase (N.E. Biolabs), 100 fmol of each oligonucleotide primer (MD073, MD074, MD075, MD077), and 500 ng of genomic DNA (extracted from homozygous β$^A$ and β$^S$ cell lines). Primers MD074 and MD077 were 5' end-labeled with [γ$^{32}$P] ATP and T4 DNA polynucleotide kinase, while primers MD073 and MD075 were 5'-phosphorylated with ATP and T4 polynucleotide kinase. As a negative control, the same reactions were performed without the target genomic DNA. The reactions were subjected to 28 LCR cycles at 94° C. for 1 minute and 62° C. for 4 minutes for one cycle followed by 94° C. for 0.5 minutes and 62° for 4 minutes for the next 27 cycles. Aliquots (5 μl) were removed from each reaction after 22 and 25 cycles. 3 μl of each reaction were mixed with 7 μl of denaturing loading buffer (90% formamide, 1×TBE, 0.1% (weight/volume) xylene cyanol, 0.1% (weight/volume) bromophenol blue) heated at 70° C. for 2 minutes and electrophoresed on a denaturing 7M urea 10% polyacrylamide gel. Quantitative analysis was performed using a Bio-Rad GS 250 Molecular Imager as per Example 1.

Results are shown in Table 3. 2'dNAD$^+$ was observed to improve the specificity of LCR reactions by reducing the ratio of mis-matched ligation to matched ligation, and the ratio of blunt-end ligation (e.g., template-independent ligation) to matched ligation was also substantially lower. Table 3 shows that the ratio of matched to mis-matched ligation improved 38.3 fold after 28 cycles of LCR by substituting 2'dNAD$^+$ for NAD$^+$ in the ligation reaction when using Taq (N.E. biolabs). Similarly, the ratio of blunt-end ligation decreased 34.5 fold after 28 cycles of LCR by substituting 2'dNAD$^+$ for NAD$^+$ in the LCR reaction.

TABLE 3

Substitution of 2'dNAD$^+$ for NAD$^+$(Example 2)*.

| Cofactor | Cycles | M** (pd**** units) | MM*** (pd units) | Ratio MM/M | ****BE (pd units) | Ratio BE/M |
|---|---|---|---|---|---|---|
| NAD$^+$ | 25 | 13848 | 5312 | 0.38 | 3284 | 0.24 |
| NAD$^+$ | 28 | 20980 | 16924 | 0.81 | 14544 | 0.69 |
| 2'-dNAD$^+$ | 25 | 4036 | 488 | 0.12 | 108 | 0.03 |
| 2'-dNAD$^+$ | 28 | 16420 | 1252 | 0.08 | 380 | 0.02 |

*Taq ligase from N.E. biolabs was used in the LCR reactions described in Table 3
**M = matched ligation
***MM = mismatched ligation
****pd = pixel density units
*****BE = blunt-end ligation Example 3: Comparison of β-2'-deoxyribose NAD$^+$ and NAD$^+$ in ligation reactions using synthetic target DNA To demonstrate that 2'dNAD$^+$ may be used as a cofactor for ligation using NAD$^+$-dependent *E. coli* DNA ligase, reactions were performed on synthetic DNA using 2'dNAD$^+$ as a cofactor. Synthetic DNA corresponding to either the normal ($\beta^A$) allele, or the sickle cell anemia ($\beta^S$) allele were used as targets for the ligation experiments. Specificity was studied by ligation of $\beta^A$ complementary oligonucleotide primers (MD075 and MD102) in the presence of both $\beta^A$ or $\beta^S$ synthetic duplex DNA templates, or by ligation of $\beta^S$ complementary oligonucleotide primers (MDO75 and MD103) in the presence of both $\beta^A$ or $\beta^S$ synthetic duplex DNA templates. Ligation reactions containing 2'dNAD$^+$ were performed in 10 μl with 20 mM Tris-HCl pH 7.9, 10 mM MgCl$_2$, 25 mM KCl, 0.1% Triton X-100, 7 fmol of $\beta^A$ template, or 7 fmol of $\beta^S$ template, 1.4 units *E. Coli* DNA ligase (N. E. Biolabs), 200 μM 2'dNAD$^+$, and 70 fmol of each $\beta^A$ or $\beta^S$ primer. A set of positive control reactions were performed using NAD$^+$ as a cofactor. Primers MD102 and MD103 were 5' end-labeled with [γ$^{32}$P] ATP and T4 Polynucleotide kinase; primer MD075 is a commercially available 5'-phosphorylated primer (M-13 Universal Primer, Operon Technologies, Alameda, Calif.). All the reagents except *E. coli* ligase were mixed and incubated at 94° C. for 2 minutes followed by a room temperature incubation for 20 minutes. Subsequently, *E. coli* DNA ligase was added and the reactions were incubated at room temperature for 30 minutes. 3 μl of each reaction were mixed with 7 μl of denaturing loading buffer (90% formamide, 1×TBE, 0.1% (w/v) xylene cyanol, 0.1% (w/v) bromphenol blue) and electrophoresed on a denaturing 7M urea 10% polyacrylamide gel. Quantitative analysis was performed with a Bio-Rad GS 250 Molecular Imager as per Example 1.

The results, which demonstrate that *E. coli* DNA ligase is competent to perform ligation in the presence of 2'dNAD$^+$ are shown in Table 4.

TABLE 4

The use of 2'dNAD$^+$ in ligation reactions with *E. coli* DNA ligase

| Template | Oligonucleotide Pair | M of MM** | 2'dNAD$^+$ |
|---|---|---|---|
| $\beta^A$ | MD075-MDO102 | M | 1608 |
| $\beta^S$ | MD075-MD102 | MM | 120 |
| $\beta^A$ | MD075-MD103 | MM | 44 |
| $\beta^S$ | MOD75-MD103 | M | 1144 |

**M = matched (base-paired) and MM = mismatched at ligation junction

Example 4: 3'-deoxyribose NAD$^+$ is a cofactor for ligation reactions.

To demonstrate that 3'dNAD$^+$ can be used as a cofactor by *E. coli* DNA ligase, synthetic DNA corresponding to either the normal ($\beta^A$) allele, or the sickle cell anemia ($\beta^S$) allele were used as targets for ligation. Specificity of ligation was studied by ligation of $\beta^A$ complementary oligonucleotide primers (MD075 and MD102) in the presence of either $\beta^A$ or $\beta^S$ synthetic duplex DNA templates, or by ligation of $\beta^S$ complementary oligonucleotide primers (MD075, and MD103) in the presence of either $\beta^A$ or $\beta^S$ synthetic duplex DNA templates. The reactions were carried out in 10 μl containing 20 mM Tris-HCl pH 7.9, 10 mM MgCl$_2$, 25 mM KCl, 0.1% Triton X-100, 7 fmol $\beta^A$ template (reactions 1 and 2) or 7 fmol $\beta^S$ template (reactions 2 and 4), 2.9 units of *E. Coli* DNA ligase (N.E. Biolabs), 200 μM 3'dNAD$^+$, 100 fmol of each $\beta^A$ primer (reactions 1 and 2) or 100 fmol of each $\beta^S$ primer (reactions 3 and 4). Positive control reactions containing NAD$^+$ were also performed. Primer MD 121 was 5' end-labeled with [γ$^{32}$P] ATP using T4 Polynucleotide kinase, and primers MD119 and MD120 were 5'-phosphorylated with ATP and T4 polynucleotide kinase. All of the reagents, except *E. coli* DNA ligase were mixed and incubated at 94° C. for 20 minutes. Subsequently, *E. coli* ligase was added and the reactions were incubated for 30 minutes at 37° C. 3 μl of each reaction were mixed with 7 μl of denaturing loading buffer (90% formamide, 1×TBE, 0.1% (w/v) xylene cyanol, 0.1% (w/v) bromphenol blue) incubated at 70° C. for 2 minutes and electrophoresed on a denaturing 7M urea/10% polyacrylamide gel. Quantitative analysis was performed using a Bio Rad GS 250 Molecular Imager as per Example 1.

The results shown in Table 5 demonstrate that *E. coli* DNA ligase is competent to perform ligation using 3'dNAD$^+$ as a cofactor.

TABLE 5

3'dNAD$^+$ as a cofactor in ligation using *E. coli* DNA ligase.

| Template | Oligonucleotide Pair | M of MM** | 3'dNAD$^+$ |
|---|---|---|---|
| $\beta^A$ | MD121-MD119 | M | 552 |
| $\beta^B$ | MD121 -MD1 19 | MM | 120 |
| $\beta^A$ | MD121-MD120 | MM | 412 |
| $\beta^B$ | MD121-MD120 | M | 428 |

**M = matched (base-paired) and MM = mismatched at ligation junction

Example 5: Relative specificity of LCR using NAD$^+$, β-2'-deoxyribose NAD$^+$ and β-3'-deoxyribose NAD$^+$ as cofactors with synthetic target DNA.

To demonstrate that 2'dNAD$^+$ and 3'dNAD$^+$ confer greater specificity than NAD$^+$ during LCR, amplification using the three cofactors was compared using Taq ligase (N.E. biolabs) to amplify a synthetic DNA target. Specificity was studied by ligation of $\beta^A$-complementary oligonucleotide primers ("A" primers) in the presence of either $\beta^A$ normal or $\beta^S$ duplex DNA templates, or by ligation of $\beta^S$-complementary oligonucleotide primers ("S" primers) in the presence of either $\beta^A$ or $\beta^S$ synthetic templates.

Three groups of reactions were carried out in 10 µl reactions containing 20 mM Tris-HCl pH 7.9, 10 mM MgCl$_2$, 25 mM KCl, 0,1% Triton X-100, 7 fmol of $\beta\beta^A$ template (group 1—reactions 1 and 3; group 2—reactions 1 and 3), or 7 fmol of $\beta^S$ template (group 1-reactions 2 and 4; group 2—reactions 2 and 4), 3.5 units of Taq Ligase (NE Biolabs), 100 fmol each of primers MD074 and MD073 ("A" primers-groups 1 and 2, reactions 1 and 2), 100 fmol each of primers MD074 and MD076 ("S" primers—groups 1 and 2, reactions 3 and 4), 200 µM 3'dNAD$^+$ (group 1), and 200 µM 2'dNAD$^+$ (group 2). Primer MD074 was 5' end-labeled with [y-$^{32}$P] ATP and T4 Polynucleotide kinase, and primers MD073, and MD076 were 5'-phosphorylated with ATP and T4 DNA polynucleotide kinase. As a control, a third set of reactions containing NAD$^+$ in place of 2'dNAD$^+$ or 3'dNAD$^+$ was performed which included the same combination and concentration of primers and templates. The third set of reactions contained 1 mM NAD$^+$, 20 mM Tris-HCl pH 7.9, 25 mM KCl, 10 mM MgCl$_2$, and 0.1% Triton X-100 The samples were placed in an Ericomp thermocycler and incubated at 94° C. for 2 minutes and then at 62° C. for 30 minutes. Subsequently, the samples (3 µl) were mixed with 7 µl of loading buffer (90% formamide, 1×TBE, 0.1% (w/v) xylene cyanol, 0.1% (w/v) bromophenol blue) and analyzed on a denaturing 10% polyacrylamide/7M urea gel. The gel was scanned with a Bio-Rad GS 250 Molecular imager and quantitated as in Example 1.

Results shown below in Table 6 demonstrate that 2'dNAD$^+$ and 3'dNAD$^+$ act as cofactors for Taq DNA ligase (N. E. Biolabs), and that the percent of mismatch ligation in the presence of 2'dNAD$^+$ and 3'dNAD$^+$ is lower than the percent of mismatch ligation observed when NAD$^+$ is used as a cofactor. For instance, when using the MD074-MD076 primer combination, the ratio of matched to mis-matched ligation using 2'dNAD$^+$ as a cofactor was 11.7 fold higher than that observed using NAD$^+$ as a cofactor. Similarly, the ratio of matched to mis-matched ligation using 3'dNAD$^+$ as a cofactor was observed to be 8.6 fold higher than the same ratio using NAD$^+$.

TABLE 6

Specificity of ligation using NAD$^+$, 2'dNAD$^+$ and 3'dNAD$^+$ in combination with Taq DNA ligase.

| Template | Oligo-nucleotide pair | M or MM** | Ligated Produce (Pixel Density Units) | | |
|---|---|---|---|---|---|
| | | | Group 3 (NAD$^+$) | Group 2 (2'dNAD$^+$) | Group 1 (3'dNAD$^+$) |
| $\beta^A$ | MD074-MD073 | M | 1432 | 1316 | 1172 |
| $\beta^S$ | MD074-MD073 | MM | 408 | 100 | 52 |
| $\beta^A$ | MD074-MD076 | MM | 1032 | 84 | 108 |
| $\beta^S$ | MD074-MD076 | M | 1880 | 1788 | 1696 |

**M = matched (base-paired) and MM = mismatched at the ligation junction.

Example 6: Specificity of LCRs using β-3'-deoxyribose NAD$^+$ as a cofactor with genomic target DNA.

Figure 4:
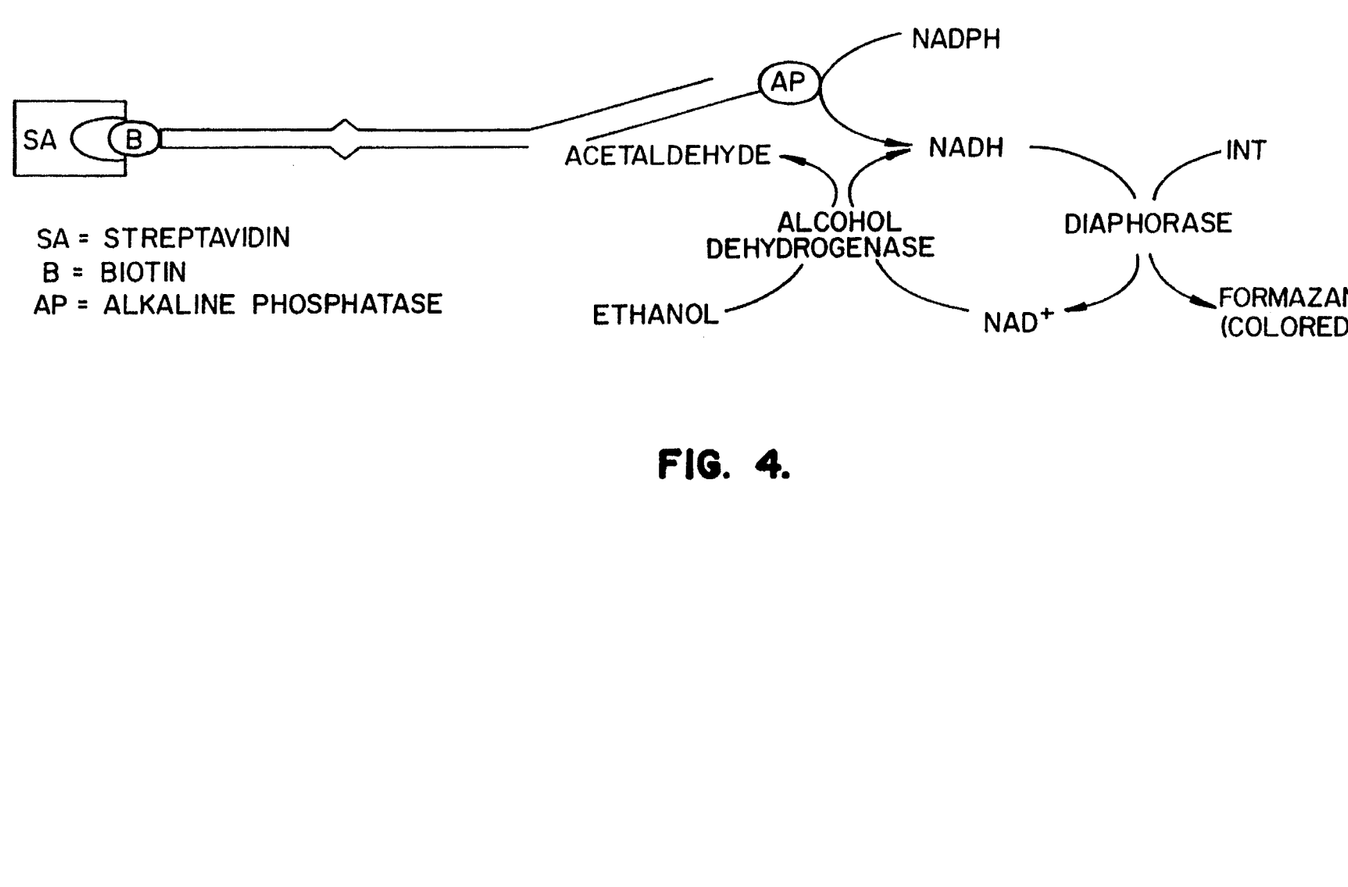
FIG. 4 describes a non-radioactive microtitre plate format for monitoring the presence of a alkaline phosphatase-labeled oligonucleotide.

To demonstrate that 3'dNAD$^+$ enhances the ability to detect differences in genomic DNA using LCR amplification, LCRs using 3'dNAD$^+$ as a cofactor were performed upon genomic DNA. The reactions were achieved by ligation of oligonucleotide primers complementary to the normal $\beta^A$ gene DNA (MD074, MD075,MD077, and MD073) in the presence of either homozygous $\beta^A$—$\beta^A$ (normal β-globin gene) or $\beta^S$—$\beta^S$ (Sickle Cell Anemia β-globin gene) genomic DNA. Reactions were performed in 25 µl volumes containing 20 mM Tris-HCl pH 7.9, 10 mM MgCl$_2$,25 mM KCl, 0.1% Triton X-100, 100 fmol of each LCR primer, 200 µM 3'dNAD$^+$, 15 units of Taq Ligase (NE Biolabs), and 500 ng of genomic DNA template (normal homozygous β-globin "AA"" or Sickle Cell Anemia β-globin "SS" genomic DNA). To check for the presence of template independent ligation, two negative controls were included. In the first control, genomic DNA isolated from an Epstein-Barr virus-transformed cell line containing a homozygous deletion for the β-globin gene ($\beta^{th}/\beta^{th}$) was used a template. In the second negative control, Salmon Sperm DNA was the target for amplification. To compare the effect of 3'dNAD$^+$ with NAD$^+$, reactions were performed in a 25 µl volume containing 20 mM Tris-HCl pH 7.6, 100 mM potassium chloride, 10 mM magnesium acetate, 10 mM DTT, 0.1% Triton X-100, 100 fmol of each LCR primer, 15 Units of Taq ligase (N.E. Biolabs), and 500 ng of genomic DNA template ("AA", "SS", $\beta^{th}/\beta^{th}$, or Salmon Sperm DNA). Both groups of reactions were subjected to 30 rounds of LCR under the following conditions: 1 round at 94° C. for 1 minutes and 4 minutes at 62° C., followed by 29 rounds at 94° C. for 0.5 minutes and 62° C. for 4 minutes. The LCR products were detected in a microtitre plate format by a non-radioactive procedure as described in FIG. 4. Briefly, one of the LCR primers complementary to the sense strand was 3'end-biotinylated and 5' end-phosphorylated, while one of the primers (MD073) complementary to the antisense strand was 5'-phosphorylated and contained a DNA tail which was complementary to an oligonucleotide labeled with alkaline phosphatase (UP-AP, commercially available from Bio-Rad, Richmond, Calif.). The UP-AP probe acts on a substrate (nicotinamide adenine phosphate (NADPH)) whose product initiates a secondary cyclic enzyme, which amplifies the initial product, producing a final colored product (Formazan).

10 µl of the LCR reactions were mixed with 40 µl of 1×SSC (0.15M sodium citrate), incubated at 37° C. for 3 hours, and then washed 5 times with 50 µl of 1×SSC/0.05% Tween-20. Subsequently, 50 µl of 1 nM UP-AP oligonucleotide (Bio-Rad Laboratories) in 1×SSC was added to the well and incubated for 1 hour at 37° C. The well was then washed 5 times with 1× SSC/0.05% Tween 20 and 50 µl of substrate (BRL Cat.#9589SA) was added and the plate was incubated for 30 minutes at 37° C. Finally, 50 µl of the amplifier was added to each well and the plate was transferred to a plate reader. The rate of color development was determined by performing a 15 minute kinetic reading at 1 minute intervals, by measuring absorbance at 490 nm.

The results shown below in Table 7 demonstrate that using 3'dNAD$^+$ as a cofactor in the LCR reaction increases substantially the specificity of ligation when the DNA which is amplified is genomic DNA. The substitution of 3'dNAD$^+$ for NAD$^+$ as a cofactor resulted in less template-independent ligation and 20 fold fewer mis-match ligation products. Thus, the added specificity enhanced the ability of one of skill to detect the genetic disorder Sickle-Cell Anemia.

TABLE 7

Example 6: 3'dNAD$^+$ enhances the detection of a genomic DNA Target.

| Template | M or MM or TI** | NAD$^+$ ($_m$OD/min) | 3'dNAD$^+$ ($_m$OD/min) |
|---|---|---|---|
| "AA" | M | 144 | 119 |
| "SS" | MM | 24 | 1 |
| β$^{th}$ β$^{th}$ | TI | 4 | 3 |
| Salmon Sperm | TI | 5 | 1 |

**M = matched ligation; MM = mismatched ligation; TI = template independent ligation Example 7: synthesis and purification of 3'-deoxyribose NAD$^+$.

The following protocol describes the method used to generate 3'-deoxyribose NAD$^+$ for use as a cofactor.

Reagents:

NAD Pyrophosphorylase and Inorganic Pyrophosphatase were obtained from (Boheringher Mannheim, Germany); Cordycepin 5' triphosphate (3'ATP), Nicotinamide Mononucleotide (NMN), Glycyl-Glycine buffer, Ammonium Acetate and Magnesium Chloride were obtained from Sigma, St. Louis, Mo.; Bio-Gel 601 was obtained from Bio-Rad Laboratories, Hercules, Calif.; TEAA (triethylamine acetate) pH 7 was obtained from Glen Research, Sterling, Va., and acetonitrile was obtained from EM Sciences, Gibbstown, N.J.

Equipment:

The High Pressure Liquid Chromatography (HPLC) System (Series 5000), equipped with dual pumps and UV detector, Bio Sil ODS (240×4 mm) C18, reversed phase HPLC column, on Econo-System for Low Pressure Chromatography equipped with a peristaltic pump, UV detector and glass column for low pressure chromatography equipped with flow adapter (1.5×10 cm) were all from Bio-Rad Laboratories, Hercules, Calif.

A 1 ml incubation mixture containing 3 mM NMN, 1 mM 3' deoxyadenosine 5' triphosphate, 0.2 units of NAD pyrophosphorylase, 3 units of inorganic pyrophosphatase, 20 mM MgCl$_2$, and 100 mM Glycyl-Glycine buffer, pH 7.4 was incubated for 16 hours (overnight) at 37° C. After incubation, 0.5 ml of 1M ammonium acetate Buffer pH 8.8 was added and the sample was applied to a glass column containing 2 ml of Bio-Gel 601 previously equilibrated with 1M ammonium acetate buffer, pH 8.8. The column was washed with 1M ammonium acetate buffer, pH 8.8, until all unbound UV absorbent material (measured at 260 nm) containing unused 3' deoxyadenosine 5' triphosphate and enzymes had eluted from the column. The column was then washed with 0.2M ammonium acetate buffer, pH 4, and the UV absorbent peak (260 nm) containing unused NMN and synthesized 3'-dNAD was collected. The collected material was applied to a ODS 5S HPLC column previously equilibrated with 0.1M TEAA buffer, pH 7. Unbound UV absorbent material (260 nm) containing unused NMN was discarded. A 30 min gradient of 0 to 25% acetonitrile was run and the (bound) peak containing pure 3' dNAD material was collected. The material eluted at approximately 20% acetonitrile. The TEAA/Acetonitrile buffer was then evaporated and the dried sample was dissolved in water. The UV absorbance was measured at 260 nm. The yield was measured by calculating the 3'dNAD concentration using an extinction coefficient of 18,500 (260 nm).

All publications and patent applications cited in this specification are herein incorporated by reference as if each individual publication or patent application were specifically and individually indicated to be incorporated by reference.

Although the foregoing invention has been described in some detail by way of illustration and example for purposes of clarity of understanding, it will be readily apparent to those of ordinary skill in the art in light of the teachings of this invention that certain changes and modifications may be made thereto without departing from the spirit or scope of the appended claims.

What is claimed is:

1. A method for ligating nucleic acid oligonucleotides, comprising the steps of:
   (a) providing a ligation reaction mixture comprising a nicotinamide adenine dinucleotide-dependent nucleic acid ligase, nucleic acid oligonucleotides, and a deoxyribose nicotinamide adenine dinucleotide, and
   (b) incubating said mixture under conditions such that said oligonucleotides are ligated to one another.

2. A method of claim 1 wherein said deoxyribose nicotinamide adenine dinucleotide is β-2'-deoxyribose nicotinamide adenine dinucleotide.

3. A method of claim 1 wherein said deoxyribose nicotinamide adenine dinucleotide is β-3'-deoxyribose nicotinamide adenine dinucleotide.

4. A method of claim 1 wherein the nucleic acid ligase is Taq DNA Ligase.

5. A method of claim 1 which further comprises the step of hybridization said nucleic acid oligonucleotides to complementary target nucleic acids prior to the addition of the nicotinamide adenine dinucleotide-dependent nucleic acid ligase to the reaction mixture.

6. A method of claim 1 wherein the nucleic acid oligonucleotides are repetitively hybridized to complementary target nucleic acids, ligated, and dissociated from the complementary nucleic acids.

7. A method of claim 1 wherein multiple sets of nucleic acid oligonucleotides are used in the ligation reaction, said sets comprising:
   (a) a set of nucleic acid oligonucleotides complementary to a target nucleic acid sequence, and
   (b) a set of nucleic acid oligonucleotides which are complementary to the nucleic acid oligonucleotides tides in (a).

8. A method of claim 6 comprising amplifying a nucleic acid in the presence of a thermostable nicotinamide adenine dinucleotide-dependant nucleic acid ligase.

9. A method for specifically ligating oligonucleotides complementary to a target polynucleotide which comprises the steps of combining in an aqueous ligation solution the target polynucleotide, nucleic acid oligonucleotides complementary to adjacent portions a deoxyribose nicotinamide adenine dinucleotide, not the target, a nicotinamide adenine dinucleotide-dependant nucleic acid ligase capable of ligating the oligonucleotides, $Mg^{++}$ and ATP; and incubating the ligation mixture to permit the nucleic acid ligase to ligate nucleic acid oligonucleotides associated with the target nucleic acid.

10. A method of claim 9, comprising the addition of β-2'-deoxyribose nicotinamide adenine dinucleotide to the aqueous ligation solution.

11. A method of claim 9 wherein the ligase is Taq DNA ligase.

12. A method of claim 9 wherein the nucleic acid oligonucleotides are hybridized to complementary target nucleic acids prior to the addition of said nicotinamide adenine dinucleotide-dependent nucleic acid ligase to the reaction mixture.

13. A method of claim 9 wherein the nucleic acid oligonucleotides are repetitively hybridized to complementary target nucleic acids, ligated, and dissociated from the complementary nucleic acids.

14. A method of claim 9 wherein multiple sets of nucleic acid oligonucleotides are used in the ligation reaction, said sets comprising:

(a) a set of nucleic acid oligonucleotides complementary to a target nucleic acid sequence, and (b) a set of nucleic acid oligonucleotides which are complementary to the nucleic acid oligonucleotides in (a).

15. A method of claim 13 comprising amplifying a nucleic acid in the presence of a thermostable nicotinamide adenine dinucleotide-dependant nucleic acid ligase.

16. A kit for ligating DNA oligonucleotides comprising a container containing an nicotinamide adenine dinucleotide-dependant DNA ligase and deoxyribose nicotinamide adenine dinucleotide.

17. The kit of claim 16, wherein the nicotinamide adenine dinucleotide-dependent DNA ligase is Taq DNA ligase.

18. The kit of claim 16, wherein the kit contains compartments containing instructional material, nicotinamide adenine dinucleotide-dependent DNA ligase, nicotinamide adenine dinucleotide and aqueous ligation buffer.

19. The kit of claim 16 wherein the kit further comprises oligonucleotides complementary to a target sequence encoding a protein which serves as a diagnostic marker for a genetic mutation.

20. The kit of claim 19 wherein the diagnostic oligonucleotides are complementary to a sequence of DNA encoding a protein which serves as a diagnostic marker for sickle-cell anemia.

* * * * *

UNITED STATES PATENT AND TRADEMARK OFFICE
CERTIFICATE OF CORRECTION

PATENT NO. : 5,508,179
DATED : Apr. 16, 1996
INVENTOR(S) : Robert B. Wallace, Hector Juarez-Salinas and Luis Ugozzoli It is certified that error appears in the above-indentified patent and that said Letters Patent is hereby corrected as shown below:

In column 8, line 29, delete "[y$^{32}$P]", and substitute therefor --[$\gamma^{32}$P]--;

In column 10, line 59, delete "[y$^{32}$P]", and substitute therefor --[$\gamma^{32}$P]--;

In column 11, line 57, delete "[y$^{32}$P]", and substitute therefor --[$\gamma^{32}$P]--, and delete "Poly- ", and substitute therefor --poly- --;

In column 12, line 37, delete "[y$^{32}$P]", and substitute therefor --[$\gamma^{32}$P]--, and delete "Polynucleotide", and substitute therefor --polynucleotide--;

In column 12, Table 5, line 58, delete "MD121-MD1 19", and substitute therefor, --MD121-MD119--;

In column 13, line 10, delete "$\beta\beta^A$", and substitute therefor, --$\beta^A$--;

In column 13, line 18, delete "[y-$^{32}$P]", and substitute therefor --[$\gamma$-$^{32}$P]--, and delete "Polynucleotide" and substitute therefor --polynucleotide--;

In column 24, line 50, delete "hybridization", and substitute therefor, --hybridizing--;

In column 25, line 8, after "portions", insert --of the target,--; and

In column 25, claim 9, line 6, delete "not the target,".

Signed and Sealed this

Twentieth Day of August, 1996

Attest:

BRUCE LEHMAN

Attesting Officer

Commissioner of Patents and Trademarks

SEQUENCE LISTING ( 1 ) GENERAL INFORMATION:

( i i i ) NUMBER OF SEQUENCES: 16

( 2 ) INFORMATION FOR SEQ ID NO:1:

( i ) SEQUENCE CHARACTERISTICS:
        ( A ) LENGTH: 21 base pairs
        ( B ) TYPE: nucleic acid
        ( C ) STRANDEDNESS: single
        ( D ) TOPOLOGY: linear     ( i i ) MOLECULE TYPE: DNA     ( i x ) FEATURE:
        ( A ) NAME/KEY: misc_feature
        ( B ) LOCATION: 1..21
        ( D ) OTHER INFORMATION: /standard_name="Primer MD074"

( x i ) SEQUENCE DESCRIPTION: SEQ ID NO:1:

ACATGGTGCA CCTGACTCCT G                                                                            2 1

( 2 ) INFORMATION FOR SEQ ID NO:2:

( i ) SEQUENCE CHARACTERISTICS:
        ( A ) LENGTH: 43 base pairs
        ( B ) TYPE: nucleic acid (C) STRANDEDNESS: single
(D) TOPOLOGY: linear (ii) MOLECULE TYPE: DNA (ix) FEATURE:
(A) NAME/KEY: misc_feature
(B) LOCATION: 1..43
(D) OTHER INFORMATION: /standard_name="Primer MD073"

(xi) SEQUENCE DESCRIPTION: SEQ ID NO:2:

AGGAGAAGTC TGCCGTTACT TTTGGCACTG GCCGTCGTTT TAC        43

(2) INFORMATION FOR SEQ ID NO:3:

(i) SEQUENCE CHARACTERISTICS:
(A) LENGTH: 22 base pairs
(B) TYPE: nucleic acid
(C) STRANDEDNESS: single
(D) TOPOLOGY: linear (ii) MOLECULE TYPE: DNA (ix) FEATURE:
(A) NAME/KEY: misc_feature
(B) LOCATION: 1..22
(D) OTHER INFORMATION: /standard_name="Primer MD075"

(xi) SEQUENCE DESCRIPTION: SEQ ID NO:3:

CAGGAGTCAG GTGCACCATG TT        22

(2) INFORMATION FOR SEQ ID NO:4:

(i) SEQUENCE CHARACTERISTICS:
(A) LENGTH: 43 base pairs
(B) TYPE: nucleic acid
(C) STRANDEDNESS: single
(D) TOPOLOGY: linear (ii) MOLECULE TYPE: DNA (ix) FEATURE:
(A) NAME/KEY: misc_feature
(B) LOCATION: 1..43
(D) OTHER INFORMATION: /standard_name="Primer MD076"

(xi) SEQUENCE DESCRIPTION: SEQ ID NO:4:

TGGAGAAGTC TGCCGTTACT TTTGGCACTG GCCGTCGTTT TAC        43

(2) INFORMATION FOR SEQ ID NO:5:

(i) SEQUENCE CHARACTERISTICS:
(A) LENGTH: 21 base pairs
(B) TYPE: nucleic acid
(C) STRANDEDNESS: single
(D) TOPOLOGY: linear (ii) MOLECULE TYPE: DNA (ix) FEATURE:
(A) NAME/KEY: misc_feature
(B) LOCATION: 1..21
(D) OTHER INFORMATION: /standard_name="Primer MD077"

(xi) SEQUENCE DESCRIPTION: SEQ ID NO:5:

CAGTAACGGC AGACTTCTCC T        21

(2) INFORMATION FOR SEQ ID NO:6:

(i) SEQUENCE CHARACTERISTICS:
(A) LENGTH: 21 base pairs
(B) TYPE: nucleic acid ( C ) STRANDEDNESS: single
            ( D ) TOPOLOGY: linear ( i i ) MOLECULE TYPE: DNA ( i x ) FEATURE:
            ( A ) NAME/KEY: misc_feature
            ( B ) LOCATION: 1..21
            ( D ) OTHER INFORMATION: /standard_name="Primer MD078"

( x i ) SEQUENCE DESCRIPTION: SEQ ID NO:6:

CAGTAACGGC AGACTTCTCC A                                    21

( 2 ) INFORMATION FOR SEQ ID NO:7:

( i ) SEQUENCE CHARACTERISTICS:
            ( A ) LENGTH: 22 base pairs
            ( B ) TYPE: nucleic acid
            ( C ) STRANDEDNESS: single
            ( D ) TOPOLOGY: linear ( i i ) MOLECULE TYPE: DNA ( i x ) FEATURE:
            ( A ) NAME/KEY: misc_feature
            ( B ) LOCATION: 1..22
            ( D ) OTHER INFORMATION: /standard_name="Primer MD119"

( x i ) SEQUENCE DESCRIPTION: SEQ ID NO:7:

AGGAGAAGTC TGCCGTTACT TT                                   22

( 2 ) INFORMATION FOR SEQ ID NO:8:

( i ) SEQUENCE CHARACTERISTICS:
            ( A ) LENGTH: 22 base pairs
            ( B ) TYPE: nucleic acid
            ( C ) STRANDEDNESS: single
            ( D ) TOPOLOGY: linear ( i i ) MOLECULE TYPE: DNA ( i x ) FEATURE:
            ( A ) NAME/KEY: misc_feature
            ( B ) LOCATION: 1..22
            ( D ) OTHER INFORMATION: /standard_name="Primer MD120"

( x i ) SEQUENCE DESCRIPTION: SEQ ID NO:8:

TGGAGAAGTC TGCCGTTACT TT                                   22

( 2 ) INFORMATION FOR SEQ ID NO:9:

( i ) SEQUENCE CHARACTERISTICS:
            ( A ) LENGTH: 43 base pairs
            ( B ) TYPE: nucleic acid
            ( C ) STRANDEDNESS: single
            ( D ) TOPOLOGY: linear ( i i ) MOLECULE TYPE: DNA ( i x ) FEATURE:
            ( A ) NAME/KEY: misc_feature
            ( B ) LOCATION: 1..43
            ( D ) OTHER INFORMATION: /standard_name="Primer MD121"

( x i ) SEQUENCE DESCRIPTION: SEQ ID NO:9:

TGGCACTGGC CGTCGTTTTA CTTCATGGTG CACCTGACTC CTG             43

( 2 ) INFORMATION FOR SEQ ID NO:10:

( i ) SEQUENCE CHARACTERISTICS:
            ( A ) LENGTH: 44 base pairs
            ( B ) TYPE: nucleic acid ( C ) STRANDEDNESS: single
( D ) TOPOLOGY: linear ( i i ) MOLECULE TYPE: DNA ( i x ) FEATURE:
    ( A ) NAME/KEY: misc_feature
    ( B ) LOCATION: 1..44
    ( D ) OTHER INFORMATION: /standard_name="Primer MD102"

( x i ) SEQUENCE DESCRIPTION: SEQ ID NO:10:

TGGCACTGGC CGTCGTTTTA CTTCACTAAC GGCAGACTTC TCCT 44

( 2 ) INFORMATION FOR SEQ ID NO:11:

( i ) SEQUENCE CHARACTERISTICS:
    ( A ) LENGTH: 44 base pairs
    ( B ) TYPE: nucleic acid
    ( C ) STRANDEDNESS: single
    ( D ) TOPOLOGY: linear ( i i ) MOLECULE TYPE: DNA ( i x ) FEATURE:
    ( A ) NAME/KEY: misc_feature
    ( B ) LOCATION: 1..44
    ( D ) OTHER INFORMATION: /standard_name="Primer MD103"

( x i ) SEQUENCE DESCRIPTION: SEQ ID NO:11:

TGGCACTGGC CGTCGTTTTA CTTCAGTAAC GGCAGACTTC TCCA 44

( 2 ) INFORMATION FOR SEQ ID NO:12:

( i ) SEQUENCE CHARACTERISTICS:
    ( A ) LENGTH: 60 base pairs
    ( B ) TYPE: nucleic acid
    ( C ) STRANDEDNESS: single
    ( D ) TOPOLOGY: linear ( i i ) MOLECULE TYPE: DNA ( i x ) FEATURE:
    ( A ) NAME/KEY: misc_feature
    ( B ) LOCATION: 1..60
    ( D ) OTHER INFORMATION: /standard_name="Primer Beta AA"

( x i ) SEQUENCE DESCRIPTION: SEQ ID NO:12:

AACAGACACC ATGGTGCACC TGACTCCTGA GGAGAAGTCT GCCGTTACTG CCCTGTGGGG 60

( 2 ) INFORMATION FOR SEQ ID NO:13:

( i ) SEQUENCE CHARACTERISTICS:
    ( A ) LENGTH: 60 base pairs
    ( B ) TYPE: nucleic acid
    ( C ) STRANDEDNESS: single
    ( D ) TOPOLOGY: linear ( i i ) MOLECULE TYPE: DNA ( i x ) FEATURE:
    ( A ) NAME/KEY: misc_feature
    ( B ) LOCATION: 1..60
    ( D ) OTHER INFORMATION: /standard_name="Primer Beta AA
        com."

( x i ) SEQUENCE DESCRIPTION: SEQ ID NO:13:

CCCCACAGGG CAGTAACGGC AGACTTCTCC TCAGGAGTCA GGTGCACCAT GGTGTCTGTT 60

( 2 ) INFORMATION FOR SEQ ID NO:14:

( i ) SEQUENCE CHARACTERISTICS:
    ( A ) LENGTH: 60 base pairs (B) TYPE: nucleic acid
(C) STRANDEDNESS: single
(D) TOPOLOGY: linear ( i i ) MOLECULE TYPE: DNA ( i x ) FEATURE:
(A) NAME/KEY: misc_feature
(B) LOCATION: 1..60
(D) OTHER INFORMATION: /standard_name="Primer Beta SS"

( x i ) SEQUENCE DESCRIPTION: SEQ ID NO:14:

AACAGACACC ATGGTGCACC TGACTCCTGT GGAGAAGTCT GCCGTTACTG CCCTGTGGGG    60

( 2 ) INFORMATION FOR SEQ ID NO:15:

( i ) SEQUENCE CHARACTERISTICS:
(A) LENGTH: 60 base pairs
(B) TYPE: nucleic acid
(C) STRANDEDNESS: single
(D) TOPOLOGY: linear ( i i ) MOLECULE TYPE: DNA ( i x ) FEATURE:
(A) NAME/KEY: misc_feature
(B) LOCATION: 1..60
(D) OTHER INFORMATION: /standard_name="Primer Beta SS com."

( x i ) SEQUENCE DESCRIPTION: SEQ ID NO:15:

CCCCACAGGG CAGTAACGGC AGACTTCTCC ACAGGAGTCA GGTGCACCAT GGTGTCTGTT    60

( 2 ) INFORMATION FOR SEQ ID NO:16:

( i ) SEQUENCE CHARACTERISTICS:
(A) LENGTH: 21 base pairs
(B) TYPE: nucleic acid
(C) STRANDEDNESS: single
(D) TOPOLOGY: linear ( i i ) MOLECULE TYPE: DNA ( i x ) FEATURE:
(A) NAME/KEY: misc_feature
(B) LOCATION: 1..21
(D) OTHER INFORMATION: /standard_name="Primer UP-AP, Available from BioRad Labs"

( x i ) SEQUENCE DESCRIPTION: SEQ ID NO:16:

GTAAAACGAC GGCCAGTGCC A    21